United States Patent
Purwar et al.

(10) Patent No.: US 11,857,805 B2
(45) Date of Patent: Jan. 2, 2024

(54) INCREASED BEAM OUTPUT AND DYNAMIC FIELD SHAPING FOR RADIOTHERAPY SYSTEM

(71) Applicant: Varian Medical Systems, Inc., Palo Alto, CA (US)

(72) Inventors: Anuj Purwar, Pleasanton, CA (US); Dragos Constantin, Los Altos, CA (US); James Clayton, San Jose, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/227,156

(22) Filed: Apr. 9, 2021

(65) Prior Publication Data
US 2021/0220674 A1  Jul. 22, 2021

Related U.S. Application Data

(63) Continuation of application No. 16/193,794, filed on Nov. 16, 2018, now Pat. No. 11,007,381.
(Continued)

(51) Int. Cl.
*A61N 5/10* (2006.01)
*H01J 35/08* (2006.01)
*H01J 35/14* (2006.01)

(52) U.S. Cl.
CPC ............ *A61N 5/1044* (2013.01); *A61N 5/10* (2013.01); *A61N 5/103* (2013.01); *A61N 5/1042* (2013.01);
(Continued)

(58) Field of Classification Search
CPC ........ A61N 5/10; A61N 5/103; A61N 5/1031; A61N 5/1042; A61N 5/1043;
(Continued)

(56) References Cited

U.S. PATENT DOCUMENTS 3,955,089 A * 5/1976 McIntyre ................ G01T 1/185
378/65
4,163,901 A 8/1979 Azam
(Continued)

FOREIGN PATENT DOCUMENTS

CN 101432739 5/2009
CN 102095852 6/2011
(Continued)

OTHER PUBLICATIONS

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.
(Continued)

*Primary Examiner* — Allen C. Ho
(74) *Attorney, Agent, or Firm* — Harness, Dickey & Pierce, P.L.C.

(57) ABSTRACT

Systems and methods provide a radiotherapy treatment by focusing an electron beam on an x-ray target (e.g., a tungsten plate) to produce a high-yield x-ray output with improved field shaping. A modified electron beam spatial distribution is employed to scan the x-ray target, such as a 2D periodic beam path, which advantageously lowers the temperature of the x-ray target compared to typical compact beam spatial distribution. As a result, the x-ray target can produce a high yield x-ray output without sacrificing the life span of the x-ray target. The use of a 2D periodic beam path allows a much colder x-ray target functioning regime such that more dosage can be applied in a short period of time compared to existing techniques.

20 Claims, 11 Drawing Sheets

Related U.S. Application Data

(60) Provisional application No. 62/587,331, filed on Nov. 16, 2017.

(52) U.S. Cl.
CPC ......... *A61N 5/1043* (2013.01); *A61N 5/1045* (2013.01); *A61N 5/1047* (2013.01); *A61N 5/1064* (2013.01); *A61N 5/1065* (2013.01); *A61N 5/1067* (2013.01); *A61N 5/1077* (2013.01); *A61N 5/1078* (2013.01); *A61N 5/1081* (2013.01); *A61N 5/1082* (2013.01); *H01J 35/116* (2019.05); *H01J 35/14* (2013.01); *A61N 2005/1074* (2013.01); *A61N 2005/1089* (2013.01); *A61N 2005/1092* (2013.01); *A61N 2005/1095* (2013.01)

(58) Field of Classification Search
CPC .. A61N 5/1044; A61N 5/1045; A61N 5/1047; A61N 5/1064; A61N 5/1065; A61N 5/1067; A61N 5/1077; A61N 5/1078; A61N 5/1081; A61N 5/1082; A61N 2005/1089; A61N 2005/1092; A61N 2005/1095
USPC .......................................................... 378/65
See application file for complete search history.

(56) References Cited

U.S. PATENT DOCUMENTS

| | | | |
|---|---|---|---|
| 4,914,681 A | 4/1990 | Klingenbeck et al. | |
| 5,153,900 A | 10/1992 | Nomikos et al. | |
| 5,267,294 A | 11/1993 | Kuroda | |
| 5,550,378 A | 8/1996 | Skillicorn et al. | |
| 5,610,967 A | 3/1997 | Moorman et al. | |
| 5,625,663 A | 4/1997 | Swerdloff et al. | |
| 5,682,412 A | 10/1997 | Skillicorn et al. | |
| 5,757,885 A | 5/1998 | Yao et al. | |
| 5,949,080 A * | 9/1999 | Ueda | G21K 5/02 378/65 |
| 6,198,802 B1 | 3/2001 | Elliott et al. | |
| 6,198,957 B1 * | 3/2001 | Green | G01R 33/4808 378/65 |
| 6,222,544 B1 | 4/2001 | Tarr et al. | |
| 6,234,671 B1 | 5/2001 | Solomon et al. | |
| 6,260,005 B1 | 7/2001 | Yang et al. | |
| 6,379,380 B1 | 4/2002 | Satz | |
| 6,411,675 B1 | 6/2002 | Llacer | |
| 6,445,766 B1 | 9/2002 | Whitham | |
| 6,504,899 B2 | 1/2003 | Pugachev et al. | |
| 6,580,940 B2 | 6/2003 | Gutman | |
| 6,993,112 B2 | 1/2006 | Hesse | |
| 7,190,764 B2 * | 3/2007 | Mori | H05H 13/08 315/111.81 |
| 7,268,358 B2 | 9/2007 | Ma et al. | |
| 7,453,983 B2 | 11/2008 | Schildkraut et al. | |
| 7,515,681 B2 | 4/2009 | Ebstein | |
| 7,522,706 B2 | 4/2009 | Lu et al. | |
| 7,560,715 B2 | 7/2009 | Pedroni | |
| 7,590,219 B2 | 9/2009 | Maurer, Jr. et al. | |
| 7,616,735 B2 | 11/2009 | Maciunas et al. | |
| 7,623,623 B2 | 11/2009 | Raanes et al. | |
| 7,778,691 B2 | 8/2010 | Zhang et al. | |
| 7,807,982 B2 | 10/2010 | Nishiuchi et al. | |
| 7,831,289 B2 | 11/2010 | Riker et al. | |
| 7,835,492 B1 | 11/2010 | Sahadevan | |
| 7,907,699 B2 | 3/2011 | Long et al. | |
| 8,284,898 B2 | 10/2012 | Ho et al. | |
| 8,306,184 B2 | 11/2012 | Chang et al. | |
| 8,401,148 B2 | 3/2013 | Lu et al. | |
| 8,406,844 B2 | 3/2013 | Ruchala et al. | |
| 8,554,302 B2 * | 10/2013 | Gross | A61B 5/055 600/411 |
| 8,559,596 B2 | 10/2013 | Thomson et al. | |
| 8,600,003 B2 | 12/2013 | Zhou et al. | |
| 8,613,694 B2 | 12/2013 | Walsh | |
| 8,636,636 B2 | 1/2014 | Shukla et al. | |
| 8,644,571 B1 | 2/2014 | Schulte et al. | |
| 8,716,663 B2 | 5/2014 | Brusasco et al. | |
| 8,831,179 B2 * | 9/2014 | Adler | H01J 35/147 378/138 |
| 8,836,332 B2 | 9/2014 | Shvartsman et al. | |
| 8,847,179 B2 | 9/2014 | Fujitaka et al. | |
| 8,903,471 B2 | 12/2014 | Heid | |
| 8,917,813 B2 | 12/2014 | Maurer, Jr. | |
| 8,948,341 B2 | 2/2015 | Beckman | |
| 8,958,864 B2 | 2/2015 | Amies et al. | |
| 8,983,573 B2 | 3/2015 | Carlone et al. | |
| 8,986,186 B2 | 3/2015 | Zhang et al. | |
| 8,992,404 B2 | 3/2015 | Graf et al. | |
| 8,995,608 B2 | 3/2015 | Zhou et al. | |
| 9,018,603 B2 | 4/2015 | Loo et al. | |
| 9,033,859 B2 | 5/2015 | Fieres et al. | |
| 9,079,027 B2 | 7/2015 | Agano et al. | |
| 9,149,656 B2 | 10/2015 | Tanabe | |
| 9,155,908 B2 | 10/2015 | Meltsner et al. | |
| 9,233,260 B2 | 1/2016 | Slatkin et al. | |
| 9,258,876 B2 | 2/2016 | Cheung et al. | |
| 9,283,406 B2 | 3/2016 | Prieels | |
| 9,308,391 B2 | 4/2016 | Liu et al. | |
| 9,330,879 B2 * | 5/2016 | Lewellen | G21K 1/025 |
| 9,333,374 B2 | 5/2016 | Iwata | |
| 9,468,777 B2 | 10/2016 | Fallone et al. | |
| 9,517,358 B2 | 12/2016 | Velthuis et al. | |
| 9,526,918 B2 | 12/2016 | Kruip | |
| 9,545,444 B2 | 1/2017 | Strober et al. | |
| 9,583,302 B2 | 2/2017 | Figueroa Saavedra et al. | |
| 9,636,381 B2 | 5/2017 | Basile | |
| 9,636,525 B1 | 5/2017 | Sahadevan | |
| 9,649,298 B2 | 5/2017 | Djonov et al. | |
| 9,656,098 B2 | 5/2017 | Goer | |
| 9,694,204 B2 | 7/2017 | Hardemark | |
| 9,719,947 B2 * | 8/2017 | Yun | G01N 23/20075 |
| 9,776,017 B2 | 10/2017 | Flynn et al. | |
| 9,786,054 B2 | 10/2017 | Taguchi et al. | |
| 9,786,093 B2 | 10/2017 | Svensson | |
| 9,786,465 B2 | 10/2017 | Li et al. | |
| 9,795,806 B2 | 10/2017 | Matsuzaki et al. | |
| 9,801,594 B2 | 10/2017 | Boyd et al. | |
| 9,844,358 B2 | 12/2017 | Wiggers et al. | |
| 9,854,662 B2 | 12/2017 | Mishin | |
| 9,874,531 B2 * | 1/2018 | Yun | H01J 35/08 |
| 9,884,206 B2 | 2/2018 | Schulte et al. | |
| 9,931,522 B2 | 4/2018 | Bharadwaj et al. | |
| 9,962,562 B2 | 5/2018 | Fahrig et al. | |
| 9,974,977 B2 | 5/2018 | Lachaine et al. | |
| 9,987,502 B1 | 6/2018 | Gattiker et al. | |
| 9,999,786 B2 * | 6/2018 | Yoshimizu | A61N 5/1065 |
| 10,007,961 B2 | 6/2018 | Grudzinski et al. | |
| 10,022,564 B2 | 7/2018 | Thieme et al. | |
| 10,071,264 B2 | 9/2018 | Liger | |
| 10,080,912 B2 | 9/2018 | Kwak et al. | |
| 10,092,774 B1 | 10/2018 | Vanderstraten et al. | |
| 10,183,179 B1 | 1/2019 | Smith et al. | |
| 10,188,875 B2 | 1/2019 | Kwak et al. | |
| 10,206,871 B2 | 2/2019 | Lin et al. | |
| 10,212,800 B2 | 2/2019 | Agustsson et al. | |
| 10,232,193 B2 | 3/2019 | Iseki | |
| 10,258,810 B2 | 4/2019 | Zwart et al. | |
| 10,272,264 B2 | 4/2019 | Ollila et al. | |
| 10,279,196 B2 | 5/2019 | West et al. | |
| 10,293,184 B2 | 5/2019 | Pishdad et al. | |
| 10,307,614 B2 | 6/2019 | Schnarr | |
| 10,307,615 B2 | 6/2019 | Ollila et al. | |
| 10,315,047 B2 | 6/2019 | Glimelius et al. | |
| 10,349,908 B2 * | 7/2019 | Yun | G01N 23/041 |
| 10,413,755 B1 | 9/2019 | Sahadevan | |
| 10,449,389 B2 | 10/2019 | Ollila et al. | |
| 10,485,988 B2 | 11/2019 | Kuusela et al. | |
| 10,525,285 B1 | 1/2020 | Friedman | |
| 10,549,117 B2 | 2/2020 | Vanderstraten et al. | |
| 10,603,514 B2 | 3/2020 | Grittani et al. | |

(56) References Cited

U.S. PATENT DOCUMENTS

| | | |
|---|---|---|
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,870,018 B2 | 12/2020 | Bartkoski et al. |
| 11,007,381 B2 | 5/2021 | Purwar et al. |
| 11,058,893 B2 * | 7/2021 | Boyd .................. A61N 5/1049 |
| 2007/0086569 A1 | 4/2007 | Johnsen |
| 2007/0287878 A1 | 12/2007 | Fantini et al. |
| 2008/0023644 A1 | 1/2008 | Pedroni |
| 2008/0088059 A1 | 4/2008 | Tang et al. |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0260662 A1 | 9/2015 | Edward et al. |
| 2015/0260663 A1 | 9/2015 | Yun et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0207425 A1 | 7/2018 | Carlton et al. |
| 2018/0236268 A1 | 8/2018 | Zwart et al. |
| 2019/0022407 A1 | 1/2019 | Abel et al. |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |

FOREIGN PATENT DOCUMENTS

| | | |
|---|---|---|
| CN | 104001270 | 8/2014 |
| CN | 106730407 | 5/2017 |
| CN | 107362464 | 11/2017 |
| CN | 109966662 | 7/2019 |
| CN | 111481840 | 8/2020 |
| CN | 111481841 | 8/2020 |
| DE | 102013206252 | 10/2014 |
| EA | 010207 | 6/2008 |
| EP | 0269927 | 6/1988 |
| EP | 0979656 | 2/2000 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 10-255707 | 9/1998 |
| JP | 2019097969 | 6/2019 |
| WO | 2006012631 | 2/2006 |
| WO | 2007017177 | 2/2007 |
| WO | 2007090650 | 8/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: a Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

(56) References Cited

OTHER PUBLICATIONS

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: a Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus on the Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/Published in final edited form as: Radiat Res. Jan. 2020; 193(1): 1-4. Published online Oct 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: the Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: a novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

(56) References Cited

OTHER PUBLICATIONS

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for.me.

Marco Durante et al., "Faster and safer? FLASH ultra-high dose rate in radiotherapy," Br J Radiol 2018; 91(1082): 20170628, British Institute of Radiology, Published Online: Dec. 15, 2017, https://doi.org/10.1259/bjr.20170628.

John R. Fischer, "PMB launches FLASH radiotherapy system for use in clinical trials," HealthCare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/S41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xlL3BpaS9zMDE2Nz gxNDAxNjMwMTcyNA==pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: a feasibility study on a digital patient," Med Phys. Nov. 2012; 39(11): 7140-7152. Published online Nov. 5, 2012. https://www.ncbi.nlm.nih.gov/pmc/articles/PMC3505203/doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects of High Energy Radiation and Ultra High Dose Rates," UMEA University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

Bw Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplements Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, P1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: a Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al, "Intensity modulated proton therapy: a clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology

(56) References Cited

OTHER PUBLICATIONS

Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for eady and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Repod 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie MA, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

\* cited by examiner

1000

1005
Determining one or more shapes and weights for treating a target region using a computer system

↓

1010
Sending control signals representing the spherical harmonic shapes from the computer system to a power management unit

↓

1015
Dynamically adjusting a current applied to steering coils using the power management unit responsive to the control signals to produce a 2D periodic path distribution of x-rays

↓

1020
Producing a resultant treatment volume of the x-rays by shaping the 2D periodic path distribution of x-rays using a beam shaping device

FIG. 10

INCREASED BEAM OUTPUT AND DYNAMIC FIELD SHAPING FOR RADIOTHERAPY SYSTEM

REFERENCE TO RELATED APPLICATIONS

This application is a continuation of U.S. Pat. No. 11,007,381 issued May 18, 2021, entitled "Increased Beam Output and Dynamic Field Shaping for Radiotherapy System," by Anuj Purwar et al., which claims the benefit of U.S. Provisional Patent Application No. 62/587,331 filed Nov. 16, 2017, entitled "Increased Beam Output and Dynamic Field Shaping," by Anuj Purwar et al., both of which are hereby incorporated herein by reference.

FIELD

Embodiments of the present invention generally relate to the field of radiotherapy. More specifically, embodiments of the present invention relate to techniques for increasing and shaping the beam output of radiotherapy systems.

BACKGROUND

A basic goal of radiotherapy treatment is the irradiation of a target volume of a patient while minimizing the amount of radiation absorbed in healthy tissue. Shaping the electron beam is an important way of minimizing the absorbed dose in healthy tissue and critical structures. Conventional collimator jaws are used for shaping a rectangular treatment field; but, as usually treatment volume is not rectangular, additional shaping is required. On a linear accelerator, lead blocks or individually made Cerrobend blocks are attached onto the treatment head under standard collimating system. Another option is the use of multileaf collimator (MLC). Multileaf collimators are becoming the main tool for beam shaping of the x-rays on the linear accelerator. It is a simple and useful system in the preparation and performance of radiotherapy treatment.

Multileaf collimators are reliable, as their manufacturers developed various mechanisms for their precision, control and reliability, together with reduction of leakage and transmission of radiation between and through the leaves. Multileaf collimators are known today as a very useful clinical system for simple field shaping, but their use is getting even more important in dynamic radiotherapy, with the leaves moving during irradiation. This enables a precise dose delivery on any part of a treated volume. Volumetric modulated arc therapy (VMAT), the therapy of the future, is based on the dynamic use of MLC.

The problem with using MLC as a field shaping device is that they are relatively slow to alter shape and therefore relatively slow to alter the field shape, e.g., the treatment volume, to the patient. It would be advantageous to provide a system with a faster field shaping response time that might reduce the overall treatment time to the patient.

Moreover, radiation treatment systems employing MLC devices typically use focused electron beams that are directed to a tungsten target to generate the x-rays. Focused electron beams create a large amount of heat on the target that must be dissipated and managed. This typically means that the incident electron beam power/dosage rate must be reduced so that the life of the target can be extended. It would be advantageous to provide a radiation treatment system that could supply a higher dose rate while still maintaining extended life of the tungsten target.

SUMMARY OF THE INVENTION

Embodiments of the present invention describe systems and methods for providing radiotherapy treatment by focusing an electron beam on a target (e.g., a tungsten plate) to produce a high-yield x-ray output with improved field shaping. A modified electron beam spatial distribution is employed to scan the target, for example, in a two-dimensional (2D) periodic path, which advantageously lowers the x-ray target temperature compared to the typical compact beam spatial distribution. As a result, the x-ray target can produce a high yield output without sacrificing the x-ray target life span. The use of a 2D periodic beam path allows a much colder target functioning regime such that more dosage can be applied in a short period of time compared to existing techniques.

In addition to reducing heat concerns on the target, the annual beam distribution on the target creates x-ray fields can be used to provide custom dose applications to a patient where the dose applications can change shape and dose distribution much faster than would otherwise be provided or possible by use of a multileaf collimator. Therefore, embodiments of the present invention provide radiotherapy in faster durations, e.g., reduced treatment times. It is appreciated that multileaf collimators (and blocks) can be used in conjunction with the x-ray fields generated via the annual beam distribution of the present invention to further shape the dose application to the patient.

According to one embodiment, a radiotherapy treatment system is disclosed, including a computer system, an electron emission device for producing and emitting an electron beam, a target, a plurality of steering coils for providing magnetic fields in perpendicular directions for steering the electron beam to the target, where the target generates x-rays responsive to interaction with the electron beam, and a beam shaping device configured to be placed between the target and a patient, the beam shaping device operable to shape a treatment volume of the x-rays. The computer system includes instructions that, when executed, cause the computer system to control the plurality of steering coils to scan the electron beam across the target in a 2D periodic path to shape the distribution of x-rays.

According to one embodiment, the electron emission device includes an electron gun and a linear accelerator coupled to receive electrons from the electron gun and operable to produce the electron beam emitted from the electron emission device.

According to one embodiment, a shape of the 2D periodic path in combination with a physical configuration and orientation of the beam shaping device defines a resultant treatment volume of x-rays exposed to the patient.

According to another embodiment, a radiotherapy treatment system is disclosed. The radiotherapy treatment system includes an electron emission device for producing and emitting an electron beam, a target, a plurality of steering coils for providing magnetic fields in perpendicular directions for steering the electron beam to the target where the target generates x-rays responsive to interaction with the electron beam, a control device coupled to the plurality of steering coils, and a beam shaping device including a multileaf collimator. The beam shaping device is configured to be placed between the target and a patient, and the beam shaping device operable to shape a treatment volume of the x-rays. The control device is operable to control the magnetic fields the plurality of steering coils to cause the electron beam to scan across the target in a 2D periodic path to produce x-rays and where further a shape of the 2D periodic path in combination with a physical configuration and orientation of the beam shaping device define a resultant treatment volume of the x-rays exposed to the patient.

According to one embodiment, the electron emission device includes an electron gun, and a linear accelerator coupled to receive electrons from the electron gun and operable to produce the electron beam, where the electron beam is of approximately 200 to 300 MeV.

According to one embodiment, the 2D periodic path includes a Lissajous type path.

According to one embodiment, the 2D periodic path includes spherical harmonic based shapes.

According to one embodiment, the spherical harmonic based shapes include a linear combination of an s-wave shape, a p-wave shape, and a d-wave shape.

According to a different embodiment, a method of generating an x-ray treatment volume using a radiotherapy treatment system is disclosed. The method includes: generating and emitting an electron beam using an electron emission device; steering the electron beam onto a target and dynamically scanning the electron beam across the target in a 2D periodic path; producing, via the target, and responsive to interaction with the electron beam being scanned thereon in accordance with the 2D periodic path, a 2D periodic distribution of x-rays; and producing a resultant treatment volume of the x-rays by shaping the 2D periodic distribution of x-rays using a beam shaping device, where a shape of the 2D periodic path in combination with a physical configuration and orientation of the beam shaping device defines the resultant treatment volume of x-rays.

According to some embodiments, the method further includes adjusting at least one of a voltage and a current over a plurality of steering coils to scan said electron beam across said target in said 2D periodic path.

According to some embodiments, the 2D periodic path comprises a convex hull.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

FIG. 10 is a flowchart depicting an exemplary sequence of computer implemented steps for automatically producing a 2D periodic distribution of x-rays from a 2D periodic electron beam path using a radiotherapy system according to embodiments of the present invention.

DETAILED DESCRIPTION

Figure 1:
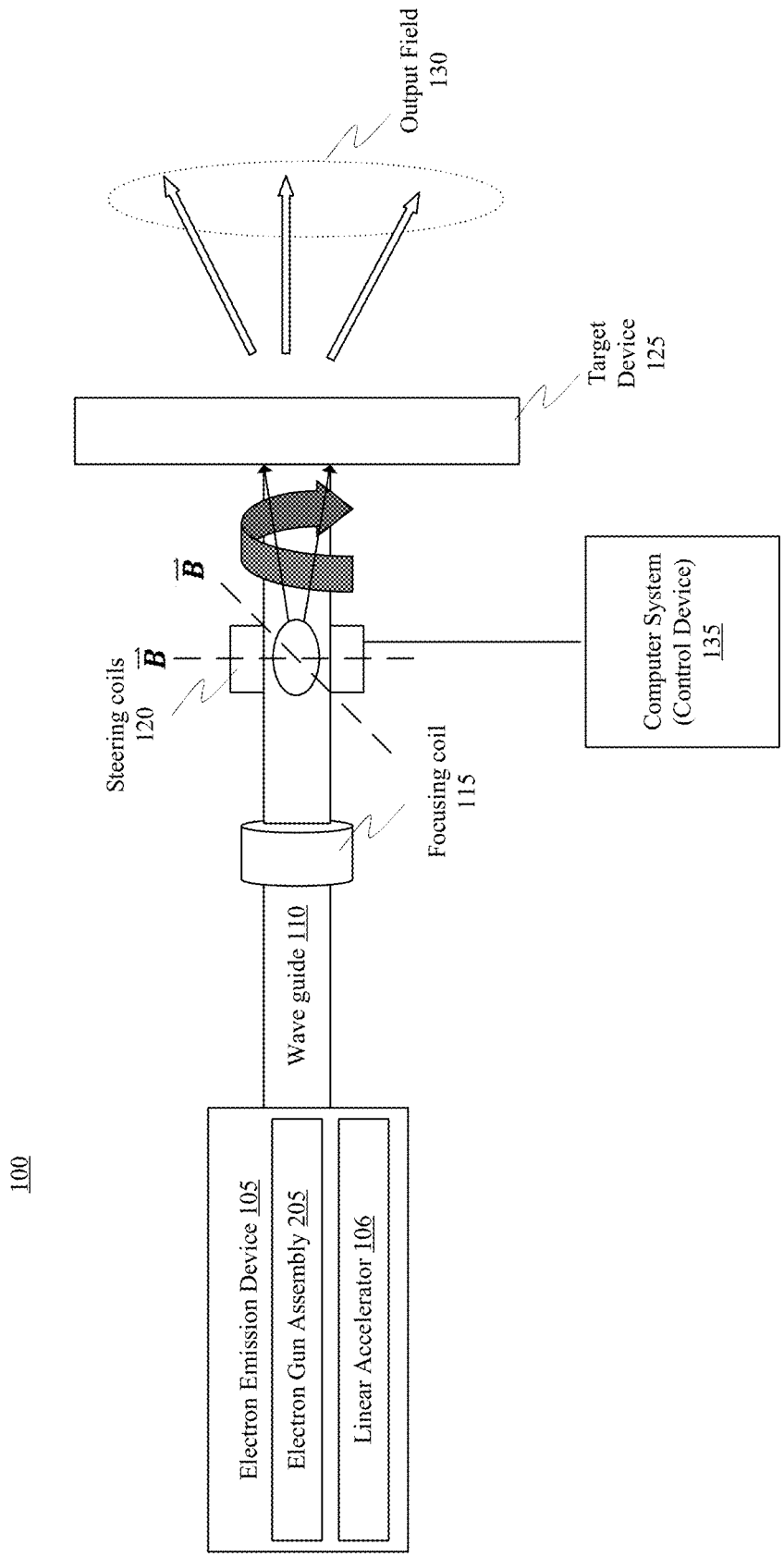
FIG. 1 depicts an exemplary radiotherapy system for scanning a 2D periodic electron beam path on a target to produce an x-ray field according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follow are presented and discussed in terms of a method. Although steps and sequencing thereof are disclosed in a figure herein (e.g., FIGS. 9 and 10) describing the operations of this method, such steps and sequencing are exemplary. Embodiments are well-suited to performing various other steps or variations of the steps recited in the flowchart of the figure herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "displaying," "writing," "including," "storing," "rendering," "transmitting," "instructing," "associating," "identifying," "capturing," "controlling," "encoding," "decoding," "monitoring," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Increased Beam Output and Dynamic Field Shaping Using a 2D Periodic Electron Beam Path Embodiments of the present invention describe systems and methods for providing radiotherapy treatment using an electron emission device that produces an electron beam focused on a target (e.g., a tungsten plate) to generate a high-yield x-ray output with improved field shaping. The high-yield x-ray output and improved field shaping minimizes the radiation received by healthy tissue, increases the dosage rate/throughput of the treatment, and increases the useful lifetime of the tungsten target.

Embodiments according to the present invention use a modified electron beam spatial distribution, such as a 2D periodic beam distribution, to lower the x-ray target temperature compared to typical compact beam spatial distribution. The temperature of the target is reduced due to the 2D periodic path of the electron beam versus a compact beam profile, e.g., the heat generated from the electron beam is spread out within the target in accordance with the beam path. As a result, the electron beam output can be increased without sacrificing x-ray target life span. The use of a 2D periodic electron beam distribution allows a much colder target functioning regime such that more dosage can be applied in a short period of time compared to existing techniques. Further, the useful life of the tungsten target is increased.

According some embodiments of the present invention, the electron beam is scanned in one or more 2D periodic paths defined by one or more predetermined elementary shapes, such as Lissajous paths or spherical harmonic based shapes (e.g., s-wave, p-wave, d-wave, and so on), in order to increase the output and shape the electron beam profile. The 2D periodic path can be rapidly dynamically altered. The elementary shapes can constitute a new basis set, as compared to the Cartesian-style basis set used for multileaf collimators (MLCs). By dynamically shaping the electron field at the target, it is possible to generate beam fluence appropriate for a tumor much faster than what an MLC can do. The MLC can still be used for leakage blocking at the edge of a field instead of primary beam shaping.

In some embodiments, the electron beam configuration is changed using external magnetic fields generated by specially designed coils. In other embodiments, hollow cathodes that generate 2D periodic beams are used, and the linear accelerator is designed such that the 2D periodic distribution is preserved along the accelerator. In yet other embodiments, existing steering coils are used to perform a scanning circular motion of the beam with a frequency higher than 200 kHz to ensure that one pulse gets smeared on the target surface in one revolution.

With regard to FIG. 1, an exemplary radiotherapy system 100 for generating a 2D periodic electron beam to the target is depicted according to embodiments of the present invention. An electron emission device 105 (e.g., an electron gun assembly 205) generates an electron beam, and a waveguide 110 transports the electron beam to a focusing coil 115 to focus the electron beam using a magnetic field. According to some embodiments, the electron emission device 105 generates an electron beam at approximately 30 kV, for example. The electron beam may be accelerated by a linear accelerator 106 to approximately 200-300 MeV in accordance with well-known techniques and equipment.

A 2D periodic distribution of x-rays is achieved, in one embodiment, using a pair of magnetic steering coils 120 to deflect the electron beam in accordance with a predetermined path on the x-ray target surface 125. The x-ray target surface 125 may be a high-yield target surface in the form of a tungsten plate or wedge, for example. As described in more detail below, the pair of magnetic steering coils 120 can be dynamically controlled to deflect the electron beam along a 2D periodic path on the x-ray target surface 125. The use of a 2D periodic electron beam distribution allows a much colder target functioning regime by dynamically moving the electron beam over a wider surface area versus a concentrated electron beam distribution. Because of this, the target output field 130 can be increased substantially without sacrificing the life span of the x-ray target surface 125. Dynamic electron beam scanning may be used to achieve a 2D periodic electron beam spatial distribution, and can also be used for dynamic field shaping by changing the scanning path using generalized curves.

The pair of magnetic steering coils 120 may include one or more pairs of magnetic steering coils that dynamically produce magnetic fields in perpendicular directions for steering the electron beam on the x-ray target surface 125. The magnetic field produced by the pair of magnetic steering coils 120 may be controlled by the computer system 135 (e.g., the computer system 1100 depicted in FIG. 11), for example, by adjusting a voltage and/or current across the pair of magnetic steering coils 120. The 2D periodic electron beam distribution may be generated by varying a voltage or current applied to the pair of magnetic steering coils 120, in combination, to produce predetermined elementary shapes, e.g., Lissajous paths or spherical harmonic based shapes (e.g., s-wave, p-wave, d-wave, and so on), or a linear combination thereof, in order to increase the output and shape the electron beam profile. The scanned 2D periodic electron beam path on x-ray target surface 125 causes to be generated an x-ray output field or distribution 130. Advantageously, this distribution 130 can be dynamically altered by corresponding dynamic adjustments of the pair of magnetic steering coils 120.

According to some alternative embodiments, the x-ray target surface 125 is not used and the radiotherapy system 100 is used to perform electron therapy.

Figure 2:
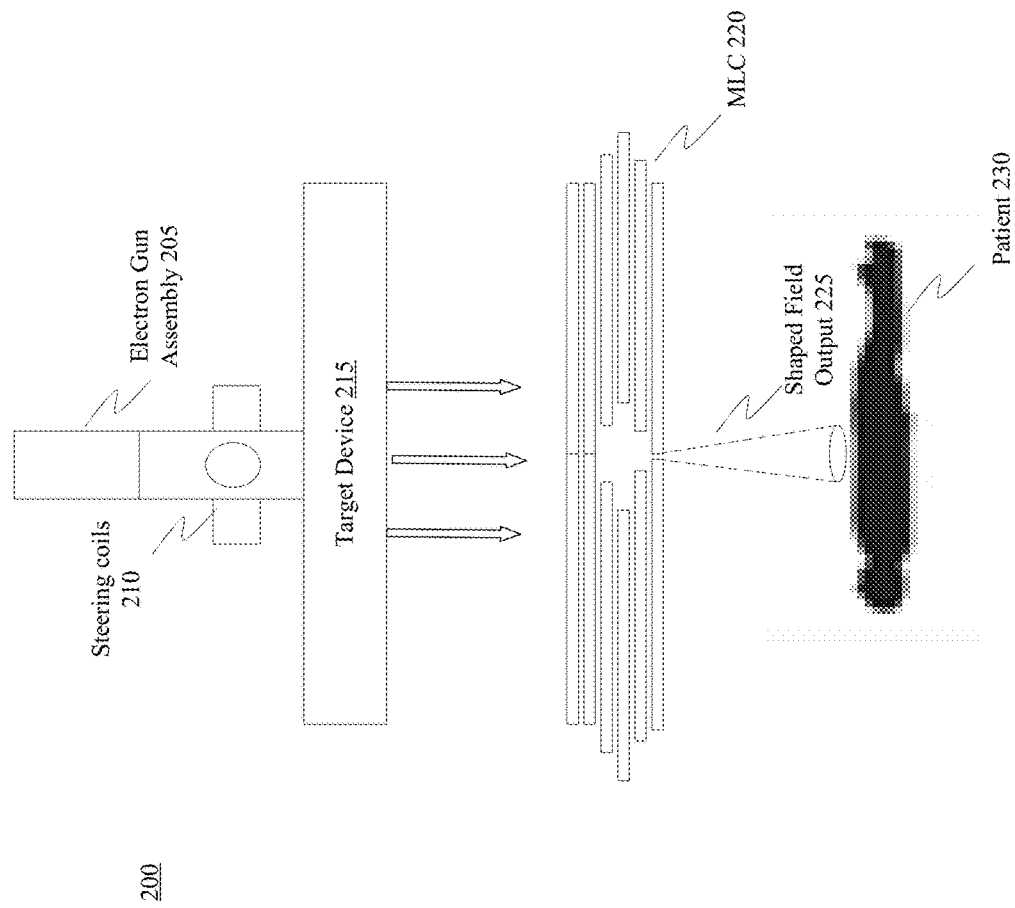
FIG. 2 depicts an exemplary radiotherapy system for generating a 2D periodic electron beam path on a target to produce x-rays shaped using a beam shaping device according to embodiments of the present invention.

In the example of FIG. 2, an exemplary radiotherapy system 200 for generating a 2D periodic electron beam to produce x-rays shaped using a beam shaping device (e.g., MLC 220) is depicted according to embodiments of the present invention. An electron gun assembly 205 generates an electron beam and a 2D periodic distribution of x-rays is achieved using a pair of magnetic steering coils 210 that generate opposed B-fields to deflect the electron beam on a 2D periodic path on the x-ray target surface 215. The use of a 2D periodic electron beam distribution allows a much colder target functioning regime such that more dosage can be applied in a shorter period of time compared to existing techniques. The MLC 220 may be used to further shape the x-ray distribution output from the x-ray target surface 215. In this fashion, the MLC 220 may be used for leakage blocking at the edge of the output field (instead of primary beam shaping). In this embodiment, the shaped field output 225 is shaped by the combination of the pair of magnetic steering coils 210 and the MLC 220, and is delivered to the target region of patient 230, for example, according to a treatment plan. In this embodiment, the dose application to the patient 230 can be altered by dynamically altering the signals to the pair of magnetic steering coils 210 as well as reconfiguration of the MLC 220. In effect, the MLC 220 can provide course shaping, and the pair of magnetic steering coils 210 can provide fine shaping, etc., or vice-versa.

Figure 3:
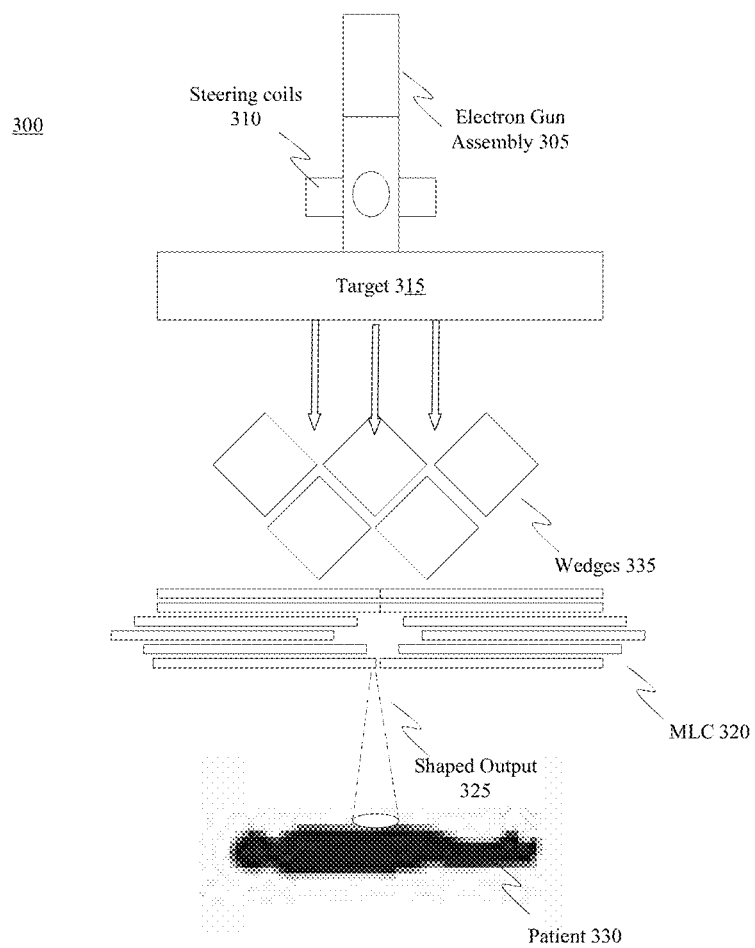
FIG. 3 depicts an exemplary radiotherapy system for generating a 2D periodic electron beam path to produce an x-ray field that is further shaped using an MLC in combination with blocks or wedges according to embodiments of the present invention.

In the embodiment of FIG. 3, an exemplary radiotherapy system 300 for generating a shaped x-ray distribution using: 1) a 2D periodic electron beam path on the x-ray target surface 315 and 2) an MLC 320 in combination with blocks or wedges 335 (e.g., lead blocks or Cerrobend blocks), is depicted according to embodiments of the present invention. An electron gun assembly 305 generates an electron beam and a 2D periodic distribution of x-rays is achieved using a pair of magnetic steering coils 310 to move the electron beam on a circular path on the x-ray target surface 315. The wedges 335 may be used to perform field shaping in addition to the MLC 320. The resultant shaped beam output 325 shaped by the pair of magnetic steering coils 310, the wedges 335, and the MLC 320 is delivered to the target region of patient 330, for example, according to a treatment plan.

Figure 4:
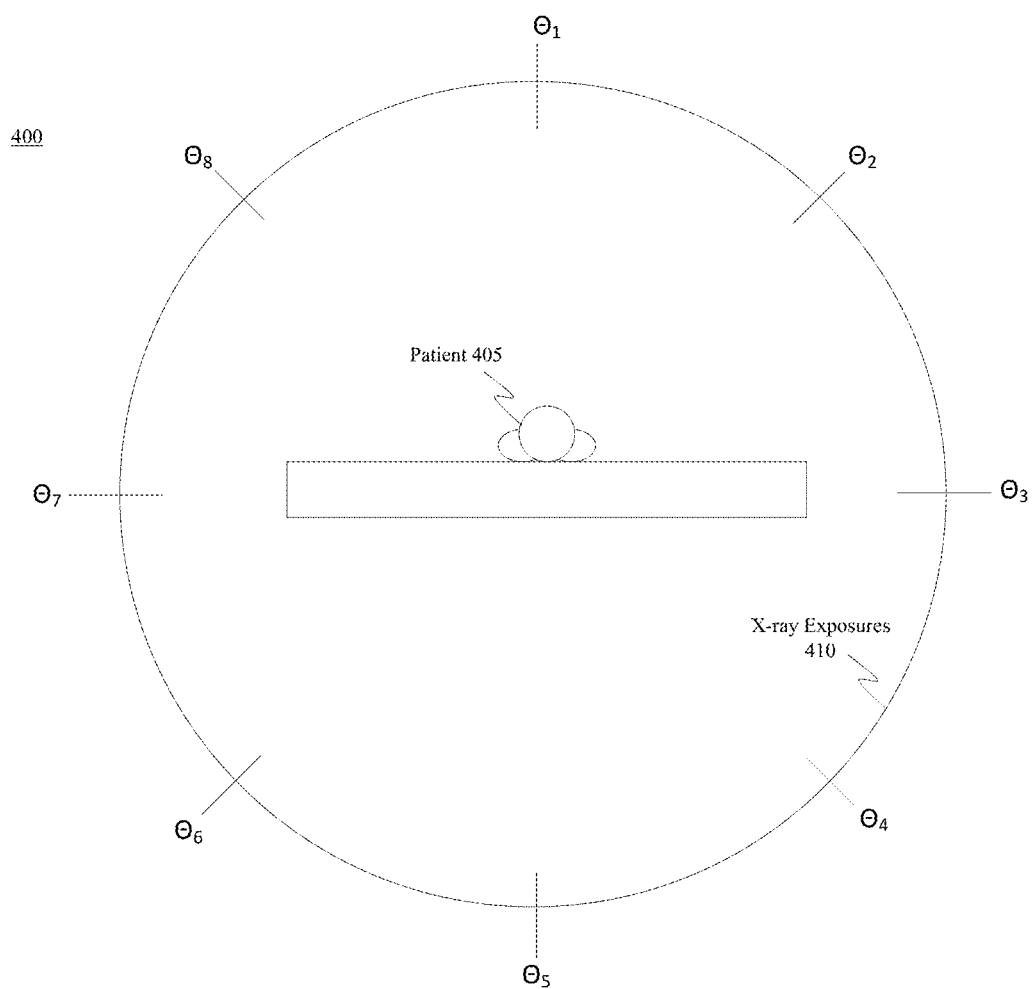
FIG. 4 depicts an exemplary tomographic patient imaging session for generating a patient treatment plan to perform radiotherapy using a 2D periodic distribution of x-rays according to embodiments of the present invention.

With regard to FIG. 4, an exemplary patient imaging session 400 for generating a patient treatment plan (e.g., a radiotherapy treatment plan) using a 2D periodic beam path is depicted according to embodiments of the present invention. The patient 405 is positioned at a center, and radiation is emitted over a computerized tomography (CT) scan configured to combine a series of x-ray exposures 410 performed over different angles (e.g., $\Theta_1$-$\Theta_8$) around the patient 405. A computer system 135 controls the radiotherapy system (e.g., of FIGS. 1-3) to radiate the patient at the different positions.

Figure 5:
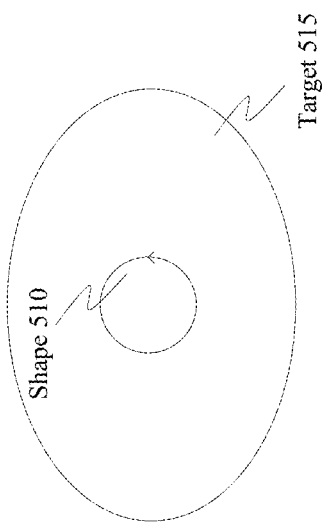
FIG. 5 depicts an exemplary circular (2D periodic) beam path generated using a pair of steering coils according to embodiments of the present invention.

FIG. 5 depicts an exemplary 2D periodic electron beam path 510 generated using a pair of magnetic steering coils as described herein according to embodiments of the present invention. The electron beam path 510 is scanned on a target 515 that generates an x-ray field for providing radiotherapy treatment. In this example, the 2D periodic beam path is roughly circular or annular.

Figure 6:
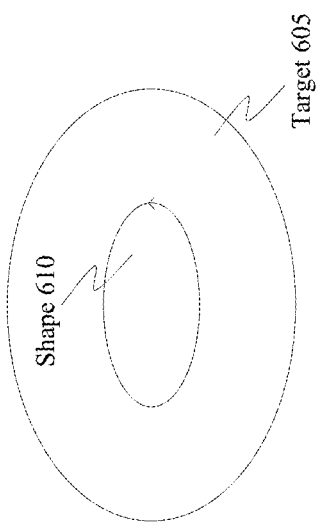
FIG. 6 depicts an exemplary elliptical (2D periodic) beam path generated using a pair of steering coils according to embodiments of the present invention.

FIG. 6 depicts an exemplary elliptical electron beam path 610 generated using a pair of magnetic steering coils as described herein according to embodiments of the present invention. The electron beam path 610 is scanned on a target 605 that generates an x-ray field for providing radiotherapy treatment.

Figure 7:
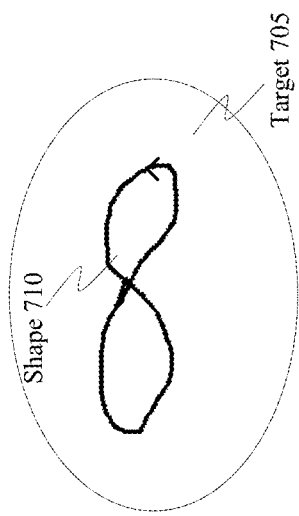
FIG. 7 depicts an exemplary figure-eight (2D periodic) beam path generated using a pair of steering coils according to embodiments of the present invention.

FIG. 7 depicts an exemplary figure-eight electron beam path 710 generated using a pair of magnetic steering coils as described herein according to embodiments of the present invention. The electron beam path 710 is scanned on a target 705 that generates an x-ray field for providing radiotherapy treatment.

According to some embodiments, electronic signals or commands are used to control a radiotherapy device for producing a corresponding beam path based on a patient's treatment plan and one or more predetermined elementary shapes (e.g., a circle, an ellipse, a figure-eight, a clover leaf, etc.). For example, multiple shapes may be selected, and each shape may be assigned a specific weight that indicates the desired beam intensity for the corresponding shape. In one example, an electronic (e.g., digital) signal or command is sent from a power management or control unit to a pair of steering coils to vary the current or voltage over the steering coils to produce a desired shape. Moving the electron beam with respect to the patient in this way reduces target heating and increases the output of the radiotherapy system. During operation, a control signal, such as an arbitrary sine wave, may be used to trigger the radiotherapy system to generate an electron beam periodically.

According to some embodiments, the electronic signals or commands are used to control a radiotherapy device for producing arbitrary 2D shapes (e.g., a convex hull) using linear combinations of basic shape functions (e.g., a circle, an ellipse, a figure-eight, a clover leaf, etc.). Moreover, tiling two-dimensional projections of a treatment volume may be optimized for Rapid Arc type treatments that rapidly deliver precise intensity modulated radiation therapy (IMRT).

Figure 8:
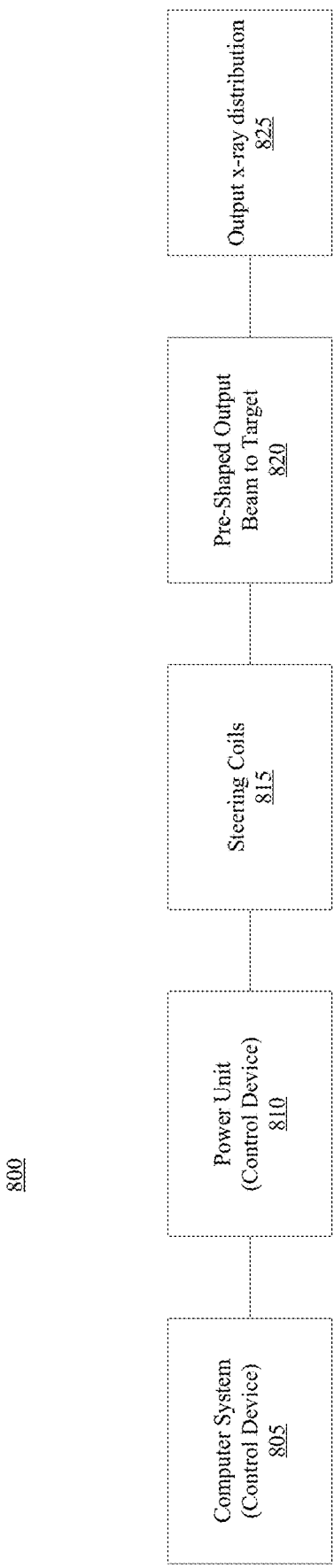
FIG. 8 depicts a block diagram and dataflow diagram of an exemplary radiotherapy treatment system for using a 2D periodic electron beam path to generate a 2D periodic field or distribution of x-rays to produce a treatment volume according to embodiments of the present invention.

As depicted in FIG. 8, according to some embodiments, a computer system 805 generates or accesses a patient treatment plan for providing radiotherapy using a radiotherapy treatment system 800. The patient treatment plan may include one or more pre-defined shapes associated with a treatment weight or magnitude. Based on the treatment plan (e.g., the shapes and weights), the computer system 805 sends one or more instructions to a power unit 810 of the radiotherapy treatment system 800 for controlling steering coils 815 of the radiotherapy treatment system 800 to generate electron beam paths according to the patient treatment plan. The power unit 810 may cause the steering coils 815 to shape the electron beam to produce the beam paths by varying a voltage or current of the control signals sent to the steering coils 810 as supplied by the power unit 810. The pre-shaped output beam is applied to a target 820 (e.g., a tungsten plate or wedge) that produces high-yield x-rays, and the resultant output x-ray distribution 825 is applied to a patient for performing radiotherapy on a target region thereof.

Figure 9:
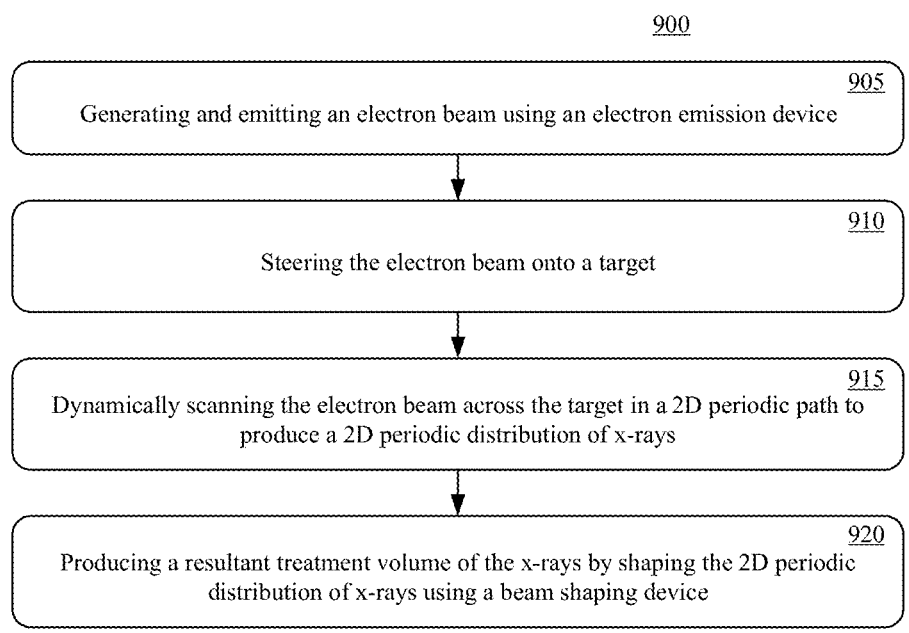
FIG. 9 is a flowchart depicting an exemplary sequence of computer implemented steps for automatically producing a 2D periodic distribution of x-rays using a 2D periodic electron beam path in a radiotherapy system according to embodiments of the present invention.

With regard to FIG. 9, an exemplary sequence of computer implemented steps 900 for automatically generating a 2D periodic beam distribution to produce a treatment volume of x-rays using a radiotherapy system is depicted according to embodiments of the present invention. At step 905, an electron beam is generated and emitted from an electron emission device, and the electron beam is steered onto a predetermined target at step 910, for example, according to a treatment plan. At step 915, the electron beam is dynamically scanned across the target in a 2D periodic path to produce a 2D periodic distribution of x-rays. At step 920, a resultant treatment volume of the x-rays is produced by shaping the 2D periodic distribution of x-rays using a beam shaping device. The resultant treatment volume generated at step 920 can provide higher dosages in a short period of time compared to existing techniques, and can extend the lifetime of the x-ray target by distributing heat across the target surface.

With regard to FIG. 10, an exemplary sequence of computer implemented steps 1000 for automatically producing a 2D periodic distribution of x-rays using a radiotherapy system is depicted according to embodiments of the present invention. At step 1005, one or more shapes (e.g., spherical harmonic shapes) and corresponding weights for treating a target region are determined using a computer system. The target region may be determined according to a treatment plan generated based on a computed tomography (CT) scan, for example. At step 1010, one or more control signals representing the shapes and weights are transmitted from the computer system to a power management unit. Thereafter, at step 1015, the power management unit dynamically adjusts a current or voltage applied to the steering coils responsive to the control signals to produce x-rays (e.g., a 2D periodic distribution of x-rays) corresponding to the shapes and the weights. At step 1020, a resultant treatment volume of the x-rays is generated by shaping the distribution of x-rays using a beam shaping device. The resultant treatment volume generated by step 1020 can provide higher dosages in a shorter period of time compared to existing techniques, and can extend the lifetime of the x-ray target by distributing heat across the target surface.

Advantageously, embodiments according to the invention can be implemented without moving parts (e.g., without moving the x-ray target). However, a 2D periodic beam distribution can be achieved by moving the x-ray target with respect to the electron beam. Moving the electron beam with respect to the target reduces target heating and increases beam output.

Figure 11:
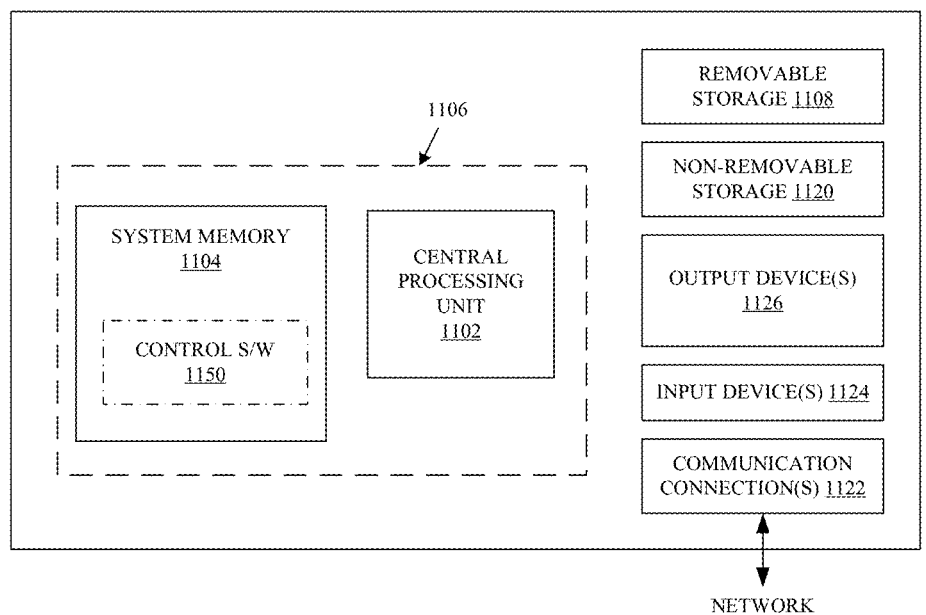
FIG. 11 shows a block diagram of an example of a computing system upon which one or more various embodiments described herein may be implemented in accordance with various embodiments of the present disclosure.

FIG. 11 shows a block diagram of an example of a computing system 1100 upon which one or more various embodiments described herein may be implemented in accordance with various embodiments of the present disclosure. The computer system 1100 may include a cloud-based computer system, a local computer system, or a hybrid computer system that includes both local and remote devices for providing radiotherapy using a 2D periodic distribution of x-rays. In a basic configuration, the computer system 1100 includes at least one processing unit 1102 and memory 1104. This basic configuration is illustrated in FIG. 11 by the dashed line 1106. The computer system 1100 may also have additional features and/or functionality. For example, the computer system 1100 may also include additional storage (e.g., removable and/or non-removable) including, but not limited to, magnetic or optical disks or tape. Such additional storage is illustrated in FIG. 11 by removable storage 1108 and non-removable storage 1120.

The computer system 1100 may also contain communications connection(s) 1122 that allow the device to communicate with other devices, e.g., in a networked environment using logical connections to one or more remote computers. Furthermore, the computer system 1100 may also include input device(s) 1124 such as, but not limited to, a voice input device, touch input device, keyboard, mouse, pen, touch input display device, etc. In addition, the computer system 1100 may also include output device(s) 1126 such as, but not limited to, a display device, speakers, printer, etc.

In the example of FIG. 11, the memory 1104 includes computer-readable instructions, data structures, program modules, and the like associated with one or more various embodiments 1150 in accordance with the present disclosure. However, the embodiment(s) 1150 may instead reside in any one of the computer storage media used by the computer system 1100, or may be distributed over some combination of the computer storage media, or may be distributed over some combination of networked computers, but is not limited to such. The computer system 1100 may be configured to generate or access a radiotherapy treatment plan and to control one or more steering coils to produce beam paths according to the radiotherapy treatment plan.

It is noted that the computer system 1100 may not include all of the elements illustrated by FIG. 11. Moreover, the computer system 1100 can be implemented to include one or more elements not illustrated by FIG. 11. It is pointed out that the computer system 1100 can be utilized or implemented in any manner similar to that described and/or shown by the present disclosure, but is not limited to such.

Embodiments of the present invention are thus described. While the present invention has been described in particular embodiments, it should be appreciated that the present invention should not be construed as limited by such embodiments, but rather construed according to the following claims.

What is claimed is:

1. A radiotherapy treatment system, comprising:
    an electron emission device configured to produce and emit an electron beam;
    a plurality of steering coils coupled to said electron emission device, and configured to produce magnetic fields in perpendicular directions for steering said electron beam; and
    a device disposed to intersect said electron beam downstream of said plurality of steering coils, wherein said plurality of steering coils are controlled to scan said electron beam in a two-dimensional (2D) periodic path, and produce a distribution of electrons across a surface of said device.

2. The radiotherapy treatment system of claim 1, wherein said device comprises a field shaping device configured to shape said distribution of electrons according to a shape of a target volume in a patient.

3. The radiotherapy treatment system of claim 1, wherein said device comprises a target device operable for generating an x-ray beam responsive to an interaction with said distribution of electrons to produce a distribution of x-rays.

4. The radiotherapy treatment system of claim 3, further comprising a field shaping device disposed downstream of said target device and configured to shape said distribution of x-rays according to a shape of a target volume in a patient.

5. The radiotherapy treatment system of claim 1, wherein said electron emission device comprises:
    an electron gun assembly; and
    a linear accelerator coupled to receive electrons from said electron gun assembly, and operable to produce said electron beam emitted from said electron emission device.

6. The radiotherapy treatment system of claim 1, wherein said 2D periodic path comprises a Lissajous-type shape.

7. The radiotherapy treatment system of claim 1, wherein said 2D periodic path comprises a spherical harmonic-based shape.

8. The radiotherapy treatment system of claim 1, wherein said 2D periodic path comprises a linear combination of an s-wave shape, a p-wave shape, and a d-wave shape.

9. The radiotherapy treatment system of claim 1, wherein said 2D periodic path comprises a non-Cartesian shape.

10. The radiotherapy treatment system of claim 1, wherein said 2D periodic path comprises a convex hull.

11. The radiotherapy treatment system of claim 1, further comprising a control device coupled to said plurality of steering coils, and operable to control said plurality of steering coils to cause said electron beam to scan in said 2D periodic path.

12. The radiotherapy treatment system of claim 1, wherein said electron beam is of a range from one MeV to 300 MeV.

13. In a radiotherapy treatment system, a method comprising:
    generating and emitting an electron beam using an electron emission device;

producing, with a plurality of steering coils, magnetic fields in perpendicular directions for steering said electron beam; and controlling said plurality of steering coils to scan said electron beam in a two-dimensional (2D) periodic path across a surface of a device downstream of said plurality of steering coils, thus producing a distribution of electrons.

14. The method of claim 13, further comprising shaping said distribution of electrons with said device according to a shape of a target volume in a patient.

15. The method of claim 13, further comprising generating an x-ray beam responsive to an interaction of said distribution of electrons with said device, thus producing a distribution of x-rays.

16. The method of claim 15, further comprising shaping said distribution of x-rays with a second device disposed between said device and a target volume, and according to a shape of said target volume.

17. The method of claim 13, wherein said 2D periodic path has a shape selected from a group consisting of: a Lissajous-type shape; a spherical harmonic-based shape; a linear combination of an s-wave shape, a p-wave shape, and a d-wave shape; a non-Cartesian shape; and a convex hull.

18. The method of claim 13, wherein said controlling comprises adjusting at least one of a voltage and a current applied to said plurality of steering coils.

19. The method of claim 13, further comprising:
selecting a plurality of shapes for said 2D periodic path; and assigning weights to said plurality of shapes, wherein each weight of said weights indicates a beam intensity for a respective shape of said plurality of shapes;

wherein said controlling comprises:
generating control signals representing said plurality of shapes and said weights; and adjusting at least one of a voltage and a current applied to said plurality of steering coils according to said control signals.

20. The method of claim 13, wherein said electron beam is of a range from one MeV to 300 MeV.

* * * * *